(12) United States Patent
Ross et al.

(10) Patent No.: US 6,512,165 B1
(45) Date of Patent: *Jan. 28, 2003

(54) METHODS FOR ENHANCING PLANT TRANSFORMATION FREQUENCIES

(75) Inventors: Margit C. Ross, Johnston, IA (US); Laura A. Church, Des Moines, IA (US); Patrea M. Hill, Des Moines, IA (US); William J. Gordon-Kamm, Urbandale, IA (US); Keith S. Lowe, Johnston, IA (US); George J. Hoerster, Des Moines, IA (US); Dennis L. Bidney, Des Moines, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/613,094

(22) Filed: Jul. 10, 2000

(51) Int. Cl.[7] .................... A01H 5/00; C12N 15/82; C12N 15/31; C12N 15/33
(52) U.S. Cl. ................ 800/290; 435/468; 800/278; 800/280; 800/288; 800/312; 800/320.1; 800/320.2; 800/320.3; 536/23.7; 536/23.72
(58) Field of Search ................ 435/468, 419; 800/278, 280, 288, 290, 312, 320.1, 314, 306, 320, 320.2, 320.3, 317.4, 317.2, 322; 536/23.7, 23.72

(56) References Cited

U.S. PATENT DOCUMENTS

| | | | |
|---|---|---|---|
| 5,741,684 A | * | 4/1998 | Fabijanski et al. |
| 6,284,947 B1 | * | 9/2001 | Gordon-Kamm et al. ............ 435/320.1 |
| 6,452,070 B1 | | 9/2002 | Gordon-Kamm et al. ... 800/290 |

FOREIGN PATENT DOCUMENTS

| | | | | |
|---|---|---|---|---|
| WO | WO 98/37184 | 8/1998 | ........... | C12N/15/00 |
| WO | WO 99/22003 | 5/1999 | ........... | C12N/15/34 |
| WO | WO 99/61619 | 12/1999 | ........... | C12N/15/29 |
| WO | WO 00/17364 | * 3/2000 | | |
| WO | WO 00/28058 | 5/2000 | ........... | C12N/15/82 |
| WO | WO 00/37645 | 6/2000 | ........... | C12N/14/29 |
| WO | WO00/50614 | 8/2000 | ........... | C12N/15/82 |

OTHER PUBLICATIONS

Mitsuhara et al, Animal cell–death suppressors Bci–xl and Ced–9 inhibit cell death in tobacco plants, Jul. 1999, Current Biology, vol. 9, pp. 775–778.*

Mittler et al, Inhibition of Programmed Cell Death in Tobacco Plants during a Pathogen–Induced Hypersensitive Response at Low Oxygen Pressure, Nov. 1996, The Plant Cell, vol. 8, pp. 1991–2001.*

Zhan et al., "The pTiC58 tzs gene promotes high–efficiency root induction by agropine strain 1855 of *Agrobacterium-rhizogenes*", *Plant Mol. Biol.* 1:785–792 (1990).

Hiei et al., "Transformation of rice mediated by *Agrobacterium tumefaciens*" *Plant Mol. Biol.* 35:205–218 (1997).

Hansen, Genevieve; "Evidence for Agrobacterium–Induced Apoptosis in Maize Cells", *Molecular Plant–Microbe Interactions*, 13(6):649–657 (2000).*

* cited by examiner

*Primary Examiner*—David T. Fox
*Assistant Examiner*—David H Kruse
(74) *Attorney, Agent, or Firm*—Pioneer Hi-Bred International, Inc.

(57) ABSTRACT

The invention provides improved plant transformation methods. In particular the method provides increased transformation freequency, especially in recalcitrant plants. The method comprises stably transforming a target cell with at least one polynucleotide of interest. The target cell has been previously transformed to stimulate growth of the cell and has gone through at least one cell division.

29 Claims, No Drawings

METHODS FOR ENHANCING PLANT TRANSFORMATION FREQUENCIES

TECHNICAL FIELD

The present invention relates generally to plant molecular biology.

BACKGROUND OF THE INVENTION

Cell division plays a crucial role during all phases of plant development. The continuation of organogenesis and growth responses to a changing environment requires precise spatial, temporal and developmental regulation of cell division activity in meristems (and in cells with the capability to form new meristems such as in lateral root formation). Such control of cell division is also important in organs themselves (i.e. separate from meristems per se), for example, in leaf expansion and secondary growth.

A complex network controls cell proliferation in eukaryotes. Various regulatory pathways communicate environmental constraints, such as nutrient availability, mitogenic signals such as growth factors or hormones, or developmental cues such as the transition from vegetative to reproductive. Ultimately, these regulatory pathways control the timing, frequency (rate), plane and position of cell divisions.

Plants have unique developmental features that distinguish them from other eukaryotes. Plant cells do not migrate, and thus only cell division, expansion and programmed cell death determine morphogenesis. Organs are formed throughout the entire life span of the plant from specialized regions called meristems.

In addition, many differentiated cells have the potential to both dedifferentiate and to reenter the cell cycle. The study of plant cell cycle control genes is expected to contribute to the understanding of these unique phenomena. O. Shaul et al., *Regulation of Cell Division in Arabidopsis, Critical Reviews in Plant Sciences*, 15(2): 97–112 (1996).

Current transformation technology provides an opportunity to engineer plants with desired traits. Major advances in plant transformation have occurred over the last few years. However, in many major crop plants, serious genotype limitations still exist. Transformation of some agronomically important crop plants continues to be both difficult and time consuming.

For example, it is difficult to obtain a culture response from some maize genotypes. Typically, a suitable culture response has been obtained by optimizing medium components and/or explant material and source. This has led to success in some genotypes. While, transformation of model genotypes is efficient, the process of introgressing transgenes into production inbreds is laborious, expensive and time consuming. It would save considerable time and money if genes could be more efficiently introduced into and evaluated directly into inbreds.

There is evidence to suggest that cells must be dividing for transformation to occur. It has also been observed that dividing cells represent only a fraction of cells that transiently express a transgene. Furthermore, the presence of damaged DNA in non-plant systems (similar to DNA introduced by particle gun or other physical means) has been well documented to rapidly induce cell cycle arrest (W. Siede, *Cell cycle arrest in response to DNA damage: lessons from yeast, Mutation Res.* 337(2:73–84). Methods for increasing the number of dividing cells would therefore provide valuable tools for increasing transformation efficiency.

Current methods for genetic engineering in maize require a specific cell type as the recipient of new DNA. These cells are found in relatively undifferentiated, rapidly growing meristems, in callus, in suspension cultures, or on the scutellar surface of the immature embryo (which gives rise to callus). Irrespective of the delivery method currently used, DNA is introduced into literally thousands of cells, yet transformants are recovered at frequencies of $10^{-5}$ relative to transiently expressing cells.

Exacerbating this problem, the trauma that accompanies DNA introduction directs recipient cells into cell cycle arrest and accumulating evidence suggests that many of these cells are directed into apoptosis or programmed cell death. (Reference Bowen et al., Tucson International Mol. Biol. Meetings). Therefore it would be desirable to provide improved methods capable of increasing transformation efficiency in a number of cell types.

While advances have been made in the transformation of elite inbreds of maize, it would be desirable to increase frequencies of transformation. Present model systems, designed around fast growing and highly embryogenic cultures, produce high frequencies of transgenic events in the hybrid GS3 and in model maize inbreds. Because of the high frequencies, these models, instead of the elite inbred genotypes, are frequently the standard target germplasm for product development.

SUMMARY OF THE INVENTION

The present invention provides a method for increasing transformation frequencies, especially in recalcitrant plants or explants. The method comprises transforming a target cell with at least one polynucleotide of interest operably linked to a promoter. The target cell has previously been stably modified to stimulate growth of the cell and has gone through at least one cell division.

DETAILED DESCRIPTION OF THE INVENTION

DEFINITIONS

As used herein "promoter" includes reference to a region of DNA upstream from the start of transcription and involved in recognition and binding of RNA polymerase and other proteins to initiate transcription.

As used herein, "polypeptide" and "protein" are used interchangeably and mean proteins, protein fragments, modified proteins, amino acid sequences and synthetic amino acid sequences. The polypeptide can be glycosylated or not.

As used herein, "polynucleotide" and "nucleic acid" are used interchangeably. A polynucleotide can be full-length or a fragment and includes polynucleotides that have been modified for stability. Unless otherwise indicated, the term includes reference to a specific sequence or its complement.

As used herein, "growth stimulation polynucleotide" means a polynucleotide capable of influencing growth of a cell. The polynucleotides fall into several categories, 1) cell cycle stimulatory polynucleotides 2) developmental polynucleotides 3) anti-apoptosis polynucleotides other than *baculovirus p35* or *baculovirus* iap 4) hormone polynucleotides or 5) silencing constructs targeted against cell cycle repressors.

The following are provided as examples of each category and are not considered a complete list of useful polynucleotides for each category: 1) cell cycle stimulatory polynucleotides including plant viral replicase genes such as RepA, Cyclins, E2F, prolifera, cdc2 and cdc25; 2) developmental polynucleotides such as Lec1, Kn1 family, WUSCHEL, Zwille, and Aintegumenta (ANT); 3) anti-apoptosis polynucleotides other than *baculovirus* p35 or *baculovirus* iap such as CED9, Bcl2, Bcl-X(L), Bcl-W, A1, McL-1, Mac1, Boo, Bax-inhibitors; 4) hormone polynucleotides such as IPT, TZS, Baby Boom (BBM) and CKI-1; 5) Silencing constructs targeted against cell cycle repressors, such as Rb, CKl, prohibitin, wee1, etc. or stimulators of apoptosis such as APAF-1, bad, bax, CED-4, caspase-3, etc. and repressors of plant developmental transitions such as Pickle and WD polycomb genes including FIE and Medea. The polynucleotides can be silenced by any known method such as antisense, cosuppression, chimerplasty, or transposon insertion.

As used herein, "growth stimulation vector" means a vector capable of altering the expression of polynucleotides resulting in growth stimulation.

As used herein, "plant" includes but is not limited to plant cells, plant tissue, plant parts, and plant seeds.

As used herein "recalcitrant plant or explant" means a plant or explant that is more difficult to transform than model systems. In maize such a model system is GS3. Elite maize inbreds are typically recalcitrant. In soybeans such model systems are Peking or Jack.

As used herein "responsive target plant cell" is a plant cell that exhibits increased transformation efficiency after transformation with a growth stimulation vector compared to a corresponding plant cell that has not been transformed with the growth stimulation vector.

As used herein "Stable Transformation" refers to the transfer of a nucleic acid fragment into a genome of a host organism (this includes both nuclear and organelle genomes) resulting in genetically stable inheritance. In addition to traditional methods, stable transformation includes the alteration of gene expression by any means including chimerplasty or transposon insertion.

As used herein "Transient Transformation" refers to the transfer of a nucleic acid fragment into the nucleus (or DNA-containing organelle) of a host organism resulting in gene expression without integration and stable inheritance.

As used herein "Modified cells" are cells that have been transformed.

As used herein "Re-transformation" refers to the transformation of a modified cell.

The present invention provides novel methods for transformation and for increasing transformation frequencies. A responsive target plant cell is stably transformed with at least one growth stimulation vector to produce a modified target cell. The modified target cell is grown under conditions to produce at least one cell division to produce a progeny cell expressing the growth stimulation vector and then the progeny cell is transformed with one or more vectors containing a polynucleotide of interest operably linked to a promoter.

In another aspect of the invention a method for increasing transformation efficiency is provided comprising transforming a target plant cell with one or more vectors containing at least one polynucleotide of interest operably linked to a promoter, wherein the target cell has been previously modified to stimulate growth of the cell and the modified cell has gone through at least one cell division.

The modified cells can be obtained from T0 transgenic cultures, regenerated plants or progeny whether grown in vivo or in vitro so long as they exhibit stimulated growth compared to a corresponding cell that does not contain the modification. This includes but is not limited to transformed callus, tissue culture, regenerated T0 plants or plant parts such as immature embryos or any subsequent progeny of T0 regenerated plants or plant parts.

Examples of polynucleotides for use in the growth stimulation vector are discussed above and include Cyclin polynucleotides such as Cyclin A, Cyclin B, Cyclin C, Cyclin D, Cyclin E, Cyclin F, Cyclin G, and Cyclin H; E2F; Cdc25; RepA and similar plant viral polynucleotides encoding replication-associated proteins; apoptosis inhibitor genes other than baculovirus p35 or baculovirus iap such as CED9, Bcl2, Bcl-X(L), Bcl-W, A1, McL-1, Mac1, Bax inhibitors, and Boo; homeotic genes or genes that stimulate in vitro growth, such as Lec1, WUS, FUS3, and members of the Knotted family, such as Kn1, STM, OSH1, and SbH1; and cytokinin genes such as IPT, TZS, CKI-1 or BBM. Polynucleotides also useful for growth stimulation include those designed to diminish expression or activity of repressors of the cell cycle such as Rb, CKI, prohibitin, wee1 or of plant development such as PICKLE or FIE (Fertilization-independent endosperm).

Polynucleotides that encode polypeptides involved in the regulation of or can influence cell cycle division in plants can be used in the growth stimulation vector. Examples include cyclins (Doerner (1994) Plant Physiol. 106:823–827.), maize cdc2 (Colasanti et al. (1991) PNAS 88:3377–3381), other cdc2 WO 99/53069, cdc25+ (Russell and Nurse (1986) Cell 45:145–153), the geminivirus RepA gene (U.S. Ser. No. 09/257,131), plant E2F (Ramirez-Parra et al. (1999) Nuc. Ac. Res. 27:3527–3533 and Sekine et al. (1999) FEBS Lett. 460:117–122), the IPT gene of *Agrobacterium tumefaciens* (Strabala et al. (1989) Mol. Gen. Genet. 216:388–394, Bonnard et al. (1989) Mol Gen. Genet. 216:428–438, DDBJ/EMBL/GenBank), TZS (Beaty et al. (1986) Mol. Gen. Genet. 203:274–280, Akiyoshi et al. (1985) Nucleic Acids Res. 13:2773–2788, Regier et al. (1989) Nucleic Acids Res. 17:8885), CKI1 (Kakimoto (1996) Science 274:982–985), BBM (Boutilier et al., Plant Mol. Biol. Reporter 18(2):S11-4 (2000) and PSKα (Yang et aL (1999) PNAS 96:13560–13565), all of which are incorporated herein by reference.

Using methods of the invention with selected proteins such as Bcl-2 (Pedoraro et al. (1984) Proc. Nat. Ac. Sci. 81 (22): 7166–7170), CED9 (Hengartner et al., Cell 76:665–676, 1994), Bcl-X(L) (Yang et al., Immunity 7:629–639, 1997), Bcl-W (Hamner et al., Neuroscience 91:673–684, 1999), A1 (Craxton et al., Cell Immunology 200:56–62, 2000), McL-1 (Akgul et al., Mol. Life Sci. 57:684–691, 2000), Mac1 Wu et al., Genbank Accession AF059715, 1999), Inohara, N., Gourley, T. S., Carrio, R., Muniz, M., Merino, J., Garcia, I., Koseki, T., Hu, Y., Chen, S. and Nunez, G., Diva, a Bcl-2 homologue that binds directly to Apaf-1 and induces BH3-independent cell death, J. Biol. Chem. 273 (49), 32479–32486 (1998), Boo (Inohara et al., J. Biol. Chem. 273:32479–32486, 1998), Bax-inhibitors (Kawai et al., FEBS Lett. 464:143–147, 1999), or IAP (inhibitor of apoptosis, see Clem et al., Trends in Cell Biol. 7:337–339; Liston et al., Nature 379:349–353, 1996; Crook et al., Journ. Vir. 67(4):2168–2174, 1993) would reduce the tendency of recently transformed cells to undergo programmed cell death, and in the process increase transgene integration and overall transformation frequencies. Using constructs designed to diminish the expression of activity of such apoptosis stimulatory genes as APAF-1, bad (Yang et al., Cell 80:285–291, 1995), bax (Han et al., Genes Dev. 10:461–477, 1996), APAF-1/CED-4 (Cecconi et al., Cell 94:727–737, 1998), caspase-3 (Fernandes-Alnemri et al., J. Biol. Chem. 269:30761–30764, 1994) would have a similar positive effect on growth enhancement and transformation, all of which are incorporated herein by reference.

Other genes useful to the invention include the Kn1 family of genes (Vollbrecht et al., Nature 350:241–243, 1991; Sentoku et al., Develop. Biol. 220:358–364, 2000), WUSCHEL (Mayer et al., Cell 95:805–815, 1998), Zwille (Moussian et al., EMBO J. 17:1799–1805, 1998), Aintegumenta (Mizukami et al., PNAS 97:942–947, 2000), prolifera (Springer et al., Science 268:877–880, 1995), PICKLE (Ogas et al., PNAS 96:13839–13844, 1999), and FIE (Ohas et al., Plant Cell 11:407–416,1999, all of which are incorporated herein by reference.

Other polynucleotides suitable for use in the growth stimulation vector include the following polynucleotides. Wee1 polynucleotides are disclosed in US99/30957 filed Dec. 21, 1999. Lec1 polynucleotides are disclosed in US99/26514 filed Nov. 9, 1999. Cyclin D polynucleotides are disclosed in WO 00/17364 published Mar. 30, 2000. CKS polynucleotides are found in 99/61619 filed May 19, 1999. DP polynucleotides are found in 09/503,139 filed Feb. 11, 2000. Cyclin E polynucleotides are found in 09/496,444 filed Feb. 2, 2000. The disclosures of these items are incorporated herein by reference.

Examples of suitable plant virus replicase polynucleotide sources include wheat dwarf virus, maize streak virus, tobacco yellow dwarf virus, tomato golden mosaic virus, abutilon mosaic virus, cassava mosaic virus, beet curly top virus, bean dwarf mosaic virus, bean golden mosaic virus, chloris striate mosaic virus, digitaria streak virus, miscanthus streak virus, maize streak virus, panicum streak virus, potato yellow mosaic virus, squash leaf curl virus, sugarcane streak virus, tomato golden mosaic virus, tomato leaf curl virus, tomato mottle virus, tobacco yellow dwarf virus, tomato yellow leaf curl virus, African cassava mosaic virus, and the bean yellow dwarf virus.

Replicase from the wheat dwarf virus has been sequenced and functionally characterized. Replicase binds to a well-characterized binding motif on the Rb protein (Xie et al., The EMBO Journal Vol. 14 no. 16 pp. 4073–4082, 1995; Orozco et al., Journal of Biological Chemistry, Vol. 272, No. 15, pp. 9840–9846, 1997; Timmermans et al., Annual Review Plant Physiology. Plant Mol. Biol, 45:79–112, 1994; Stanley, Genetics and Development 3:91–96, 1996; Davies et al., *Geminivirus Genomes,* Chapter 2, and Gutierrez, Plant Biology 1:492–497, 1998). The disclosures of these items are incorporated herein by reference.

Other polynucleotides suitable for use in the growth stimulation vector include viral cell cycle modulator proteins such as CLINK (Aronson et al. Journal of Virology 74: 2968–2972, 2000). The disclosure of which is incorporated herein by reference. Examples of other viral sources for this type of protein include banana bunchy top virus, milk vetch dwarf virus, subterranean color stunt virus Ageratum yellow vein virus and other representatives of plant nanoviruses.

Repressors of plant developmental transitions such as Pickle and WED polycomb genes including FIE and Medea can be used in the practice of the invention (Ohad et al. *Plant Cell* 1999 Mar. 11 (3):407–416; et al. *Plant Cell* 1999 May 11(3):765–768; *Curr Biol* 2000 Jan 27:10(2)R71–74; Curr Biol 1998 Jul 2:8(14)R480–484; Science 1998 Apr 17:280 (5362) 446–450), all of which are incorporated herein by reference.

The growth stimulation polynucleotides can be attached to a vector, adapter, promoter, transit peptide or linker for cloning and/or expression of a polynucleotide suitable for use in the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The construction of expression cassettes that can be employed in conjunction with the present invention is well known to those of skill in the art in light of the present disclosure. See, e.g., Sambrook, et al.; *Molecular Cloning: A Laboratory Manual;* Cold Spring Harbor, N.Y.; (1989); Gelvin, et al.; *Plant Molecular Biology Manual;* (1990); *Plant Biotechnology: Commercial Prospects and Problems,* eds. Prakash, et al.; Oxford & IBH Publishing Co.: New Delhi, India; (1993); and Heslot, et al.; *Molecular Biology and Genetic Engineerinq of Yeasts;* CRC Press, Inc., USA; (1992); each incorporated herein in its entirety by reference.

For example, expression cassettes may include (1) a growth stimulation polynucleotide under the transcriptional control of 5' and 3' regulatory sequences and (2) a dominant selectable marker. Such expression cassettes may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens,* the ubiquitin 1 promoter (Christensen et al., Plant Mol. Biol 18:675–689, 1992), the Smas promoter (REF), the cinnamyl alcohol dehydrogenase promoter (U.S. Pat. No. 5,683,439), the Nos promoter (Shaw et al., Nucl. Acids Res. 12:7831–7846, 1984), the pEmu promoter (Last et al, Theor. Applied Genet. 81:581–588, 1991), the rubisco promoter (Gittins et al., Planta 210:232–240, 2000), the GRP1-8 promoter and other transcription initiation regions from various plant genes known to those of skill.

Examples of inducible promoters are the Adh1 promoter which is inducible by hypoxia or cold stress (Walker et al., PNAS 84:6624–6628, 1987), the Hsp70 promoter which is inducible by heat stress (Rochester et al., EMBO J. 5:451–458, 1986), and the PPDK promoter which is inducible by light (Nomura et al., Plant J. 22:211–221, 2000). Also useful are promoters that are chemically inducible.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; *Plant Sci.* 47, 95–102 (1986) and Reina, M., Ponte, I., Guillen, P., Boronat, A. and Palau, J., Sequence analysis of a genomic clone encoding a Zc2 protein from Zea mays W64 A, *Nucleic Acids Res.* 18 (21), 6426 (1990). See the following site relating to the waxy promoter: Kloesgen, R. B., Gierl, A., Schwarz-Sommer, ZS. and Saedler, H., Molecular analysis of the waxy locus of Zea mays, *Mol. Gen. Genet.* 203, 237–244 (1986). Promoters that express in the embryo, pericarp, and endosperm are disclosed in U.S. applications Ser. Nos. 60/097,233 filed Aug. 20, 1998 and 60/098,230 filed Aug. 28, 1998. The disclosures each of these are incorporated herein by reference in their entirety.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, *Mol. Cell Biol.* 8:4395–4405 (1988); Callis et al., *Genes Dev.* 1:1183–1200 (1987). Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

The vector comprising the polynucleotide sequences useful in the present invention may comprise a marker gene that confers a selectable phenotype on plant cells. Usually, the selectable marker gene will encode antibiotic or herbicide resistance. Suitable genes include those coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of nucleic acids in higher plants are well known in the art and include vectors derived from the tumor-inducing (Ti) plasmid of *Agrobacterium tumefaciens* described by Rogers et al., Meth. In Enzymol., 153:253–277 (1987). Exemplary *A. tumefaciens* vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.). A variety of plant viruses that can be employed as vectors are known in the art and include cauliflower mosaic virus (CaMV), geminivirus, brome mosaic virus, and tobacco mosaic virus.

The growth stimulation polynucleotide can be expressed in either sense or anti-sense orientation as desired. In plant cells, it has been shown that antisense RNA inhibits gene expression by preventing the accumulation of mRNA which encodes the enzyme of interest, see, e.g., Sheehy et al., *Proc. Nat'l. Acad. Sci. (USA)* 85: 8805–8809 (1988); and Hiatt et al., U.S. Pat. No. 4,801,340.

Another method of suppression is sense suppression. For an example of the use of this method to modulate expression of endogenous genes see, Napoli et al., The Plant Cell 2: 279–289 (1990) and U.S. Pat. No. 5,034,323. Another method of down-regulation of the protein involves using PEST sequences that provide a target for degradation of the protein. Still other methods of suppression are disclosed in WO 99/53050, which discloses a method that involves both sense and antisense suppression, i.e. hairpin technology.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

The methods of the present invention can be used with any cell such as bacteria, yeast, insect, non-human mammalian, or preferably plant cells.

Typically, an intermediate host cell will be used in the practice of this invention to increase the copy number of the cloning vector. With an increased copy number, the vector containing the nucleic acid of interest can be isolated in significant quantities for introduction into the desired plant cells. Host cells that can be used in the practice of this invention include prokaryotes, including bacterial hosts such as *Eschedcia coli, Salmonella typhimurium,* and *Serratia marcescens.* Eukaryotic hosts such as yeast or filamentous fungi may also be used in this invention. It preferred to use plant promoters that do not cause expression of the polypeptide in bacteria.

Commonly used prokaryotic control sequences include promoters such as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using *Bacillus* sp. and Salmonella (Palva, et al., *Gene* 22: 229–235 (1983); Mosbach, et al., *Nature* 302: 543–545 (1983)).

The invention can be practiced in a wide range of plants such as monocots or dicots. For example, the methods of the present invention can be employed in corn, soybean, sunflower, safflower, potato, tomato, sorghum, canola, wheat, alfalfa, cotton, rice, barley and millet.

The method of transformation is not critical to the invention; various methods of transformation are currently available. As newer methods are available to transform host cells they may be directly applied. Accordingly, a wide variety of methods have been developed to insert a DNA sequence into the genome of a host cell to obtain the transcription and/or translation of the sequence. Thus, any method that provides for efficient transformation/transfection may be employed.

A DNA sequence coding for the desired polynucleotide useful in the present invention, for example a cDNA, RNA or a genomic sequence, will be used to construct an expression cassette that can be introduced into the desired host cell. Isolated nucleic acid acids useful in the present invention can be introduced into plants according techniques known in the art. Generally, expression cassettes as described above and suitable for transformation of plant cells are prepared.

Methods for transforming various host cells are disclosed in Klein et al. "Transformation of microbes, plants and animals by particle bombardment", Bio/Technol. New York, N.Y., Nature Publishing Company, March 1992, v. 10 (3) pp. 286–291. Techniques for transforming a wide variety of higher plant species are well known and described in the technical, scientific, and patent literature. See, for example, Weising et al., Ann. Rev. Genet. 22: 421–477 (1988).

For example, the DNA construct may be introduced directly into the genomic DNA of the plant cell using techniques such as electroporation, PEG-mediated transfection, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp.197–213 in Plant Cell, Tissue and Organ Culture, Fundamental Methods. eds. O. L. Gamborg and G. C. Phillips. Springer-Verlag Berlin Heidelberg New York, 1995. The introduction of DNA constructs using polyethylene glycol precipitation is described in Paszkowski et al., *Embo J.* 3: 2717–2722 (1984). Electroporation techniques are described in Fromm et al., *Proc. Natl. Acad. Sci.* 82: 5824 (1985). Ballistic transformation techniques are described in Klein et al., *Nature* 327: 70–73 (1987).

Alternatively, the DNA constructs may be combined with suitable T-DNA flanking regions and introduced into a conventional *Agrobacterium tumefaciens* host vector. The virulence functions of the Agrobacterium tumefaciens host will direct the insertion of the construct and adjacent marker into the plant cell DNA when the cell is infected by the bacteria. *Agrobacterium tumefaciens*-meditated transformation techniques are well described in the scientific literature. See, for example Horsch et al., *Science* 233: 496–498 (1984), and Fraley et al., *Proc. Natl. Acad. Sci.* 80: 4803 (1983). For instance, Agrobacterum transformation of maize is described in U.S. Pat. No. 5,981,840. Agrobactedum transformation of monocot is found in U.S. Pat. No. 5,591,616. Agrobacterum transformation of soybeans is described in U.S. Pat. No. 5,563,055.

Other methods of transformation include (1) *Agrobactedum rhizogenes*-mediated transformation (see, e.g., Lichtenstein and Fuller In: Genetic Engineering, vol. 6, PWJ Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., Plant Cell Physiol. 25: 1353, 1984), (3) the vortexing method (see, e.g., Kindle, *Proc. Natl. Acad. Sci., USA* 87: 1228, (1990).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plane Mol. Biol. Reporter, 6:165 (1988). Expression of polypeptide coding nucleic acids can be obtained by injection of the DNA into reproductive organs of a plant as described by Pena et al., Nature, 325.:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp.27–54 (1986).

Animal and lower eukaryotic (e.g., yeast) host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology,* Dowden, Hutchinson and Ross, Inc. (1977).

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For transformation and regeneration of maize see, Gordon-Kamm et al., The Plant Cell, 2:603–618 (1990).

Once the responsive target cell is transformed with the growth stimulation polynucleotide, it is re-transformed with a gene of interest. The transformed cell can be from transformed callus, transformed embryo, T0 regenerated plants or its parts, progeny of T0 plants or parts thereof as long as the growth stimulation polynucleotide is present.

Genes of interest can include any gene, generally, those involved in oil, starch, protein, carbohydrate or nutrient metabolism as well as those affecting kernel size, sucrose loading, and the like. The gene of interest may be involved in regulating the influx of nutrients, disease resistance and in regulating expression of phytate genes particularly to lower phytate levels in the seed.

General categories of genes of interest for the purpose of present invention include for example, those genes involved in information, such as Zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, and grain characteristics. It is recognized that any gene of interest can be operably linked to the promoter of the invention and expressed in the seed.

Important traits such as oil, starch and protein content can be genetically altered. Modifications include altering the content of oleic acid, saturated and unsaturated oils, increasing levels of lysine and sulfur-containing amino acids and providing other essential amino acids, and also modification of starch and cellulose. Hordothionin protein modifications are described in WO94/16078; WO96/38562; WO96/08220; and U.S. Pat. No. 5,703,409 issued Dec. 30, 1997 the disclosures of which are incorporated herein in their entirety by reference. Another example is lysine and/or sulfur rich seed protein encoded by the soybean 2S albumin described in WO97/35023, and the chymotrypsin inhibitor from barley, Williamson et al. (1987) Eur. J. Biochem. 165:99–106, the disclosures of each are incorporated by reference.

Derivatives of the following genes can be made by site directed mutagenesis to increase the level of preselected amino acids in the encoded polypeptide. For example, the gene encoding the barley high lysine polypeptide (BHL) is derived from barley chymotrypsin inhibitor, WO98/20133, incorporated herein by reference. Other proteins include methionine-rich plant proteins such as from sunflower seed (Lilley et al. (1989) Proceedings of the World Congress on Vegetable Protein Utilization in Human Foods and Animal Feedstuffs; Applewhite, H. (ed.); American Oil Chemists Soc., Champaign, Ill.: pp. 497–502, incorporated herein in its entirety by reference), corn (Pedersen et al. (1986) J. Biol. Chem. 261:6279; Kirihara et al. (1988) Gene 71:359, both incorporated herein in its entirety by reference) and rice (Musumura et al. (1989) Plant Mol. Biol. 12:123, incorporated herein in its entirety by reference). Other agronomically important genes encode Floury 2, growth factors, seed storage factors and transcription factors.

Commercial traits can also be encoded on a gene(s) which could alter or increase for example, starch for the production of paper, textiles, and ethanol, or provide expression of proteins with other commercial uses. Another important commercial use of transformed plants is the production of polymers and bioplastics such as described in U.S. Pat. No. 5,602,321 issued Feb. 11, 1997. Genes such as B-ketothiolase, PHBase (polyhydroxyburyrate synthase) and acetoacetyl-CoA reductase (see Schubert et al. (1988) J. Bacteriol 170(12):5837–5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of seed proteins, particularly modified seed proteins having improved amino acid distribution to improve the nutrient value of the seed can be increased. This is achieved by the expression of such proteins having enhanced amino acid content.

Insect resistance genes may encode resistance to pests that have great yield drag such as rootworm, cutworm, European Corn Borer, and the like. Such genes include, for example, *Bacillus thuringiensis endotoxin* genes (U.S. Pat. Nos. 5,366,892; 5,747,450; 5,737,514; 5,723,756; 5,593,881; Geiser et al. (1986) Gene 48:109); lectins (Van Damme et al. (1994) Plant Mol. Biol. 24:825); and the like.

Genes encoding disease resistance traits may include detoxification genes, such as against fumonosin (U.S. patent application No. 08/484,815 filed Jun. 7, 1995); avirulence (avr) and disease resistance (R) genes (Jones et al. (1994) Science 266:789; Martin et al. (1993) Science 262:1432; Mindrinos et al. (1994) Cell 78:1089; and the like.

Agronomic traits in seeds can be improved by altering expression of genes that affect the response of seed growth and development during environmental stress, Cheikh-N et al. (1994) Plant Physiol. 106(1):45–51) and genes controlling carbohydrate metabolism to reduce kernel abortion in maize, Zinselmeier et al. (1995) Plant Physiol. 107(2):385–391.

The gene of interest or the growth stimulation polynucleotide may be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired response. Thus the promoter sequences disclosed herein may be operably linked to antisense DNA sequences to reduce or inhibit expression of a native protein in the plant seed.

Transformed plants cells can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture,* Macmillan Publishing Company, New York, pp. 124–176 (1983); and Binding, *Regeneration of Plants, Plant Protoplasts,* CRC Press, Boca Raton, pp. 21–73 (1985).

The regeneration of plants containing the foreign gene introduced by Agrobacterium can be achieved as described by Horsch et al., *Science,* 227:1229–1231 (1985) and Fraley et al., *Proc. Natl. Acad. Sci. U.S.A.,* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38: 467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, *The Maize Handbook,* Freeling and Walbot, Eds., Springer, New York (1994); *Corn and Corn Improvement,* $3_{rd}$ edition, Sprague and Dudley Eds., American Society of Agronomy, Madison, Wisconsin (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self-crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention. Progeny and variants, and mutants of the regenerated plants are also included within the scope of the invention, provided that these parts comprise the introduced nucleic acid sequences.

Transgenic plants expressing a selectable marker can be screened for transmission of the gene(s) of interest, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes.

The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Seeds derived from plants regenerated from re-transformed plant cells, plant parts or plant tissues, or progeny derived from the regenerated plants, may be used directly as feed or food, or further processing may occur.

Through the integration of a gene or genes into the elite (recalcitrant) maize inbreds whose stable expression might have a positive influence on transformation, the following data demonstrate potential in increasing the overall genetic transformation throughput of elite maize germplasm. It is expected that integration for re-transformation with other genes or gene combinations will further improve the elite inbred transformation frequency.

The present invention will be further described by reference to the following detailed examples. It is understood, however, that there are many extensions, variations, and modifications on the basic theme of the present invention beyond that shown in the examples and description, which are within the spirit and scope of the present invention.

All publications, patents, and patent applications cited herein are hereby incorporated by reference.

EXAMPLES

Example 1.

DNA Delivery Methods

Transformation of the Lec1 plasmids, PHP16102, PHP16215, and PHP16273 along with the expression cassette UBI::moPAT-GPFm::pinII into genotype Hi-II followed a well-established bombardment transformation protocol used for introducing DNA into the scutellum of immature maize embryos (Songstad, D. D. et al., In Vitro Cell Dev. Biol. Plant 32:179–183, 1996). It is noted that any suitable method of transformation can be used, such as Agrobacterium-mediated transformation and many other methods. Cells were transformed by culturing maize immature embryos (approximately 1–1.5mm in length) onto medium containing N6 salts, Erikkson's vitamins, 0,69 g/l proline, 2 mg/l 2,4-D and 3% sucrose. After 4–5 days of incubation in the dark at 28° C., embryos were removed from the first medium and cultured onto similar medium containing 12% sucrose. Embryos were allowed to acclimate to this medium for 3 h prior to transformation. The scutellar surface of the immature embryos was targeted using particle bombardment. Embryos were transformed using the PDS-1000 Helium Gun from Bio-Rad at one shot per sample using 650PSI rupture disks. DNA delivered per shot averaged at 0.1667 $\mu$g. Following bombardment, all embryos were maintained on standard maize culture medium (N6 salts, Erikkson's vitamins, 0.69 g/l proline, 2 mg/l 2,4-D, 3% sucrose) for 2–3 days and then transferred to N6-based medium containing 3 mg/L Bialaphos®. Plates were maintained at 28° C. in the dark and were observed for colony recovery with transfers to fresh medium every two to three weeks. Recovered colonies and plants were scored based on GFP visual expression, leaf painting sensitivity to a 1% application of Ignite® herbicide, and molecular characterization via PCR and Southern analysis.

Transformation of the RepA containing plasmid (PHP15524) and control plasmid (PHP15325) into Pioneer Hi-Bred International, Inc. proprietary maize inbreds N46 and P38 were done using the Agrobacterium mediated DNA delivery method, as described by U.S. Pat. No. 5,981,840 with the following modifications. It is noted that any suitable method of transformation can be used, such as particle-mediated transformation, as well as many other methods. Agrobacteria were grown to the log phase in liquid minimal A medium containing 100 $\mu$M spectinomycin. Embryos were immersed in a log phase suspension of Agrobacteria adjusted to obtain an effective concentration of $5 \times 10^8$ cfu/ml. Embryos were infected for 5 minutes and then co-cultured on culture medium containing acetosyringone for 7 days at 20° C. in the dark. After 7 days, the embryos were transferred to standard culture medium (MS salts with N6 macronutrients, 1 mg/L 2,4-D, 1 mg/L Dicamba, 20 g/L sucrose, 0.6 g/L glucose, 1 mg/L silver nitrate, and 100 mg/L carbenicillin) with 3 mg/L Bialaphos® as the selective agent. Plates were maintained at 28° C. in the dark and were observed for colony recovery with transfers to fresh medium every two to three weeks. Recovered colonies and plants were scored based on GFP visual expression, leaf painting sensitivity to a 1% application of Ignite® herbicide, and molecular characterization via PCR and Southern analysis.

Example 2.

Re-transformation of RepA transgenic progeny results in increased transformation frequency in elite maize inbreds The plasmids listed in the table below were used to evaluate the influence of RepA on stable expression of co-delivered transgenes. Two vectors were constructed to test the repA gene constructs using Agrobacterium-mediated transformation. A control vector, designated PHP15303, carried two gene cassettes. The first comprised a ubiquitin promoter:intron sequence driving a Green Fluorescent Protein (GFP) coding sequence. This coding sequence had previously been modified to optimize codons for expression in maize and to include an intron (precluding expression of the GFP in bacterial cells). A polyadenylation signal sequence from the pinII gene was used. The second gene in this vector was the selectable marker CaMV35S Enhancer:CaMV35S promoter:Omega Prime 5'UTR:ADH1 intron1: BAR:pinII. This control vector was mated into *Agrobactenium tumefaciens* LBA4404 carrying a superbinary vir plasmid (PHP10523). The resulting 15303/10523 cointegrate plasmid was designated PHP15325.

The second vector was derived from the wheat dwarf virus (WDV) promoter:replicase gene originally obtained from Jo Messing (pWI-11). The myb region of the rep Exon 2 was deleted (as a 130 bp Asp700 fragment) to create plasmid PHP14807 (WDV promoter:REP-EXON1 :REP-INTRON1 :REP-EXON2 (Asp700 DELETION):WDV TERM). This expression cassette was cloned into a polylinker in an intermediate vector to pick up flanking BstEII sites. The cassette was then moved as a 1.93 kb BstEII fragment into compatible BstEll sites in PHP15303 just upstream of the two genes described above. This three-gene plasmid was designated PHP15440. After mating into *Agrobacterium tumefaciens* LBA4404 carrying a superbinary vir plasmid (PHP10523) as above, the final 15440/10523 cointegrate plasmid was designated PHP15524.

TABLE 1

| Plasmid | Description |
|---------|-------------|
| P15325 | RB/e35S::BAR::PinII + Ubi::Ubi intron::GFPm::PinII/LB |
| P15524 | RB/e35S::BAR::PinII + Ubi::Ubi intron::GFPm::PinII + wdv LIR::RepA(ASP700)/LB |

The visible marker gene GFP (green fluorescence protein; Chalfie, et al., Science 263:802, 1994) has been described as has the maize-optimized GFP (GFPm; see copending U.S. patent application WO 97/41228). The Ubiquitin promoter has been described (Christensen et al., Plant Mol. Biol. 12: 619–623 (1989) and Christensen etal., Plant Mol. Biol. 18: 675-689 (1992), as has the pinII (An et al., 1989, Plant Cell 1: 115–122) 3' region used in these cassettes.

Transformations of the RepA containing plasmid (P15524) and control plasmid (P15325) in maize inbreds P38 and N46 were done using the Agrobacterium mediated DNA delivery method, as described by U.S. Pat. No. 5,981,840 with modifications as listed in Example 1. Embryos were co-cultured on culture medium with acetosyringone for 7 days at 20° C. After 7 days the embryos were transferred to standard culture medium containing 3mg/L Bialaphos with the addition of 100 mg/L carbenicillin to kill off residual Agrobacteria. Total embryos cultured per ear were divided between the two plasmids to evaluate the effect of RepA on inbred transformation. Fertile plants with normal phenotypes were recovered based on reporter gene expression, leaf resistance to herbicide, and molecular analyses in both RepA events and in control events containing only BAR and GFPm.

A study was initiated to evaluate if the integrated RepA transgene from these events would have any effect on the frequency of subsequent transformations. $T_1$ embryos from both RepA and control events were selected. Ears to be harvested were infused at 4DAP with compounds found to yield optimal embryogenic response within the genotype (U.S. Ser. No. 09/425,510), harvested at 10DAP, and bombarded using the particle gun following the methodology listed in Example 1. The visual marker CRC was used as the transgene for this study. The marker was put into vector PHP7951, containing the nos promoter driving the CRC transgene with a PinII terminator. CRC has been previously described (Bruce, W. et al., Plant Cell 12:65–79, 2000). CRC expressing sectors were recovered at high frequencies without selective pressure across independent events only from the embryos segregating for the RepA transgene (based on GFPm expression). Wild type segregates as well as control events containing only the selectable marker and reporter gene did not yield high frequencies of transformation (Table II). These data demonstrate that RepA expression improves re-transformation frequencies.

TABLE II

Maize Elite Inbred Re-Transformation Data

| Event SID | Genotype | DNA | # Embryos | # GPF+ | # CRC+ | Overall Frequency | Segregated Frequency |
|-----------|----------|-----|-----------|--------|--------|-------------------|----------------------|
| RepA Integrated: | | | | | | | |
| 1025332 | P38 | P15524 | 24 | 14 | 1 | 4.2% | 7.1% |
| 1025341 | P38 | P15524 | 72 | 41 | 14 | 19.4% | 34% |
| 1028139 | P38 | P15524 | 21 | 3 | 0 | 0% | 0% |
| 1052134 | N46 | P15524 | 15 | 6 | 4 | 29% | 66% |
| 1038724 | N46 | P15524 | 150 | 1 | 18 | 12% | 100% |
| 1052136 | N46 | P15524 | 42 | 18 | 2 | 5% | 11.1% |
| Controls: | | | | | | | |
| 1027793 | P38 | P15325 | 98 | 6 | 0 | 0 | 0 |
| 1033190 | P38 | P15325 | 60 | 25 | 0 | 0 | 0 |
| 1025793 | P38 | P15325 | 60 | N/A | 0 | 0 | 0 |
| 1045751 | P38 | P15325 | 7 | 5 | 0 | 0 | 0 |
| 1025334 | P38 | P15325 | 94 | 38 | 1 (died) | 0 | 0 |
| 1029080 | P38 | P15325 | 196 | 98 | 1 | 0.5% | 1% |
| 1025723 | P38 | P15325 | 160 | 67 | 0 | 0 | 0 |
| 1029082 | P38 | P15325 | 30 | 11 | 0 | 0 | 0 |

P15524: RB/e35S::BAR::PinII + Ubi::Ubi intron::GFPm intron::PinII + wdv::RepA (ASP700)/LB
P15325: RB/e35S::BAR::PinII + Ubi::Ubi intron::GPFm intron::PinII/LB Example 3.

Validation of Re-transformation of RepA transgenic progeny results in increased transformation frequency in elite maize inbreds To further evaluate the effect of the integrated RepA transgene on maize inbred transformation, $T_1$ seed from RepA (PHP15524) events were planted from genotypes N46 and P38. Wild type seed were also planted to serve as transformation controls. The T1 plants were screened to identify segregates for the RepA transgene, and outcrossed to their wild type recurrent parent or other elite inbreds PH24E and PH09B. A group (both Ti and controls) of the ears produced were infused at 4DAP (U.S. Ser. No. 09/425, 510) with compounds found to yield optimal embryogenic response within the genotype and harvested for immature embryo transformation. Transformations were completed using the Agrobacterium mediated DNA delivery method, as described by U.S. Pat. No. 5,981,840 with modifications as listed in Example 1. Total embryos cultured per ear were divided between the plasmids PHP16543, containing the visual marker CRC, as described above, and PHP16340. containing the Rice EPSPS gene conferring resistance to glyphosate, as described in Table III below:

TABLE III

| Plasmid | Description |
|---------|-------------|
| PHP16543 | RB/NOS-C(G)RC-PinII + Ubi-moPAT-35S/LB |
| PHP16340 | RB/RiceEPSPS pro-eMPU-e35S-RiceEPSPS intron-Rice EPSPS-Rice EPSPS term/LB |

All embryos were co-cultured on culture medium with acetosyringone for 7 days at 20° C. After 7 days, the embryos were transferred to standard culture medium with the addition of 100 mg/L carbenicillin and either no selective agent (for transformations done with PHP16543) or 0.25 mM glyphosate (for transformations done with PHP16340). After 7 weeks, embryos were evaluated for normal growth on glyphosate selection or stable anthocyanin expression. Transformation frequencies (to date based on the embryos available for scoring) are as shown in Table IV below. Parent genotype P38 was transformed with RepA to produce T0 transformant 1023702. Transformant 1023702 was crossed with P38 to produce T1 progeny 1133200. Parent genotype P38 was transformed with RepA to produce T0 transformant 1025298. Transformant 1025298 was crossed with P38 to produce T1 progeny 1133131, 1133132, 1133133,1133137, and 1133161. Parent genotype N46 was transformed with RepA to produce T0 transformant 1033131. Transformant 1033131 was crossed with N46 to produce T1 progeny 1133064, 1133067, 1133088, 1133082, 1133103.

TABLE IV

| T1 Cross or Wild Type Control | Parent Genotype (s) | Parent SID | DNA | # Embryos | # Expressing Colonies | Overall Frequency |
|---|---|---|---|---|---|---|
| P38 ear 1 wild type | P38 | N/A | PHP16340 | 21 | 0 | 0% |
| P38 ear 1 wild type | P38 | N/A | PHP16543 | 21 | 1 | 4.8% |
| P38 ear 2 wild type | P38 | N/A | PHP16340 | 4 | 0 | 0% |
| P38 ear 2 wild type | P38 | N/A | PHP16543 | 2 | 0 | 0% |
| PH09B, ear 1 wild type | PH09B | N/A | PHP16340 | 30 | 0 | 0% |
| PH09B, ear 1 wild type | PH09B | N/A | PHP16543 | 29 | 0 | 0% |
| PH24E, ear 1 wild type | PH24E | N/A | PHP16340 | 23 | 0 | 0% |
| PH24E, ear 1 wild type | PH24E | N/A | PHP16543 | 31 | 0 | 0% |
| PH24E, ear 2 wild type | PH24E | N/A | PHP16340 | 23 | 0 | 0% |
| PH24E, ear 2 wild type | PH24E | N/A | PHP16543 | 22 | 0 | 0% |
| PH24E/1133200 | PH24E and P38 | 1023702 | PHP16340 | 40 | 2 | 5% |
| PH24E/1133200 | PH24E and P38 | 1023702 | PHP16543 | 34 | 2 | 5.9% |
| 1133131/P38 | P38 | 1025298 | PHP16340 | 32 | 19 | 59.4% |
| 1133131/P38 | P38 | 1025298 | PHP16543 | 28 | 6 | 21.4% |
| 1133132/P38 | P38 | 1025298 | PHP16340 | 70 | 5 | 7.1% |
| 1133132/P38 | P38 | 1025298 | PHP16543 | 8 | 8 | 8.04% |
| 1133133/P38 | P38 | 1025298 | PHP16340 | 42 | 6 | 14.3% |
| 1133133/P38 | P38 | 1025298 | PHP16543 | 11 | 1 | 9.1% |
| 1133161/P38 | P38 | 1025298 | PHP16340 | 19 | 5 | 26.3% |
| 1133161/P38 | P38 | 1025298 | PHP16543 | 42 | 0 | 0% |
| PH09B/1133137 | PH09B and P38 | 1025298 | PHP16340 | 41 | 4 | 9.8% |
| PH09B/1133137 | PH09B and P38 | 1025298 | PHP16543 | 45 | 1 | 2.2% |
| 1133064/N46 | N46 | 1033131 | PHP16340 | 32 | 2 | 6.3% |
| 1133064/N46 | N46 | 1033131 | PHP16543 | 41 | 2 | 4.9% |
| 1133067/N46 | N46 | 1033131 | PHP16340 | 36 | 2 | 5.5% |
| 1133067/N46 | N46 | 1033131 | PHP16543 | 16 | 0 | 0% |
| 1133068/N46 | N46 | 1033131 | PHP16340 | 11 | 4 | 36.6% |
| 1133068/N46 | N46 | 1033131 | PHP16543 | 16 | 1 | 6.3% |
| 1133082/N46 | N46 | 1033131 | PHP16340 | 44 | 5 | 11.4% |
| 1133082/N46 | N46 | 1033131 | PHP16543 | 47 | 2 | 4.3% |
| 1133103/N46 | N46 | 1033131 | PHP16340 | 9 | 4 | 44.4% |
| 1133103/N46 | N46 | 1033131 | PHP16543 | 13 | 1 | 7.7% |

The level of glyphosate selection used in this study was determined to be optimal for eliminating any wild type growth from maize embryos based on kill curve studies done using ranges of glyphosate from 0.01 mM to 2 mM. Genotypes P38, PH24E, and PH09B were evaluated.

Pending molecular confirmation data for segregation ratios for RepA and for the newly transformed transgenes, and based on visual inspection of GPFm expression, it is predicted that the above transformations will correspond to the data produced in the previous example; RepA expression improves re-transformation frequencies in inbreds.

Example 4.

Re-transformation of LECI-transgenic progeny results in elevated transformation frequency in Hi-II.

Agrobacterium mediated transformation

As the starting point for Agrobacterium-mediated re-transformation experiments, regenerated Hi-II T0 transformants were produced containing maize LEC1 expression cassettes and UBI::moPAT~GFP::pinII. The LEC1 expression cassettes used the nopaline synthase promoter from *Agrobacterium tumefaciens* (Shaw et al., Nucl. Acids Res. 12:7831–7846, 1984) or modified nos promoters as described below. The PAT~GFP cassette contained a maize-optimized gene encoding phosphinothricin acetyltransferase (moPAT, see co-Pending Application WO9830701) followed by a sequence encoding 4x(GSSS) to create a flexible polypeptide linker, and then a maize-optimized nucleic acid sequence encoding Green Fluorescence Protein (GFP; see co-Pending Application WO 97/41228 published Nov. 6, 1997). This PAT~GFP fusion construct was driven by the maize ubiquitin promoter (Christensen et al., Plant Mol. Biol. 18:675–689, 1992) and contains a potato proteinase inhibitor II 3' sequence (An et al., Plant Cell 1:115–122, 1989). Transformants containing UBI::moPAT~GFP::pinII and one of three different LEC1 expression cassettes were tested; with LEC1 being driven by a nos promoter (PHP16102), a truncated version containing 85 bases of the nos sequence (PHP16215), or a nos promoter with additional STOP codons added before the START in order to attenuate expression (PHP16273).

Transgenic Hi-II plants containing a co-segregating LEC1 expression cassette and the UBI::PAT~GFP expression cassette were crossed to wild-type (non-transformed) Hi-II plants (using the non-transformed parent as the pollen donor). As expected from such a cross, the developing embryos on these ears segregated either for transgene expression or wild-type. Immature embryos were harvested 12 days after pollination and transformed with an Agrobacterium binary plasmid containing PHP16449 (UBI::moCAH::pinII, moCAH is a maize optimized [for codon usage] gene that encodes for the *Myrothecium verrucaria* cyanamide hydratase protein[CAH] that can hydrate cyanamide to non-toxic urea). A standard Agrobacterium-mediated transformation protocol (U.S. Pat. No. 5,981,840) adapted for cyanamide selection (see WO 9830701) was used, with additional modifications listed below. Agrobacterium was grown to log phase in liquid minimal-A medium containing 100 μM acetosyringone and spectinomycin. Embryos were immersed in a log phase suspension of Agrobacterium adjusted to obtain $3 \times 10^8$ CFU's/ml. Embryos were then co-cultured on culture medium with acetosyringone for 3 days at 20° C. After 3 days the embryos were returned to standard culture medium with 100 mg/l carbinicillin added to kill residual Agrobacterium. After an additional 4 days the segregating embryos were divided into GFP positive and GFP negative populations and moved to fresh culture medium with 50 mg/l cyanamide for selection. After 8 weeks the numbers of transformed colonies were determined.

The results are summarized in the table below. Since the PAT~GFP and LEC1 expression cassettes were co-segregating, GFP expression was used to separate segregating transgenic (PAT~GFP+/LEC1+) and non-transgenic (wild-type) embryos after Agrobacterium-mediated transformation, and then these separate populations were cultured and selected as independent groups. Using embryos from three different ears co-segregating for GFP and LEC1, the LEC1-containing embryos exhibited a much higher transformation frequency demonstrating that ectopic LEC1 expression improves retransformation frequencies. Wild-type embryos (non-transgenic segregants) from two ears did not produce transformants, while the LEC1-containing embryos from the same ears produced cyanimide-resistant transformants at approximately a 8.5% frequency. In the third ear harvested and tested in this manner, moCAH transformants were recovered at a 11.8% frequency for the wild-type embryos, while for the LEC1 embryos from the same ear the transformation frequency increased to 33.8%.

TABLE V

| T0 transgenes (co-Ear segregating) | # GFP + embryos | # of GFP − embryos | Tnx. Frequency GFP + embryos | Tnx. Frequency GFP − embryos |
|---|---|---|---|---|
| 1 PHP16215 + GFP | 68 | 68 | 23/68 = 33.8% | 8/68 = 11.8% |
| 2 PHP16102 + GFP | 47 | 70 | 4/47 = 8.5% | 0/70 |
| 3 PHP16273 + GFP | 34 | 22 | 3/34 = 8.8% | 0/22 |

Particle gun transformation re-transformations

As the starting point for particle gun-mediated retransformation experiments, regenerated Hi-II T0 transformants were produced containing maize LEC1 expression cassettes and UBI::moPAT~GFP::pinII. Transformants containing UBI::moPAT~GFP::pinII and LEC1 expression cassettes were tested; with LEC1 being driven by a nos promoter with additional STOP codons added before the START in order to attenuate expression (PHP16273), and a truncated version of the nos promoter containing 85 bases of the nos sequence (PHP16215). As a control, a non-functional version of LEC1 was used, in which the LEC1 coding sequence was frame-shifted by 1 position after the START codon, resulting in essentially the same mRNA species but producing a non-functional protein. Expression of this frame-shifted sequence (abbreviated "f-shift" below) was driven by the In2 promoter (PHP15636). As mentioned above for the functional LEC1 genes, this f-shift LEC1 cassette co-segregated with GFP in the T1 progeny embryos.

Transgenic Hi-II plants containing a co-segregating LEC1 expression cassette and the UBI::PAT~GFP expression cassette were crossed to wild-type (non-transformed) Hi-II plants (using the non-transformed parent as the pollen donor). As expected from such a cross, the developing embryos on these ears segregated either for transgene expression or wild-type. Embryos co-segregating for GFP and LEC1 (functional and frame-shift versions) were transformed using a particle gun using the standard Hi-II bombardment transformation protocol (Songstad D. D. et al., In Vitro Cell Dev. Biol. Plant 32:179–183, 1996). Cells were transformed by culturing maize immature embryos (approximately 1–1.5mm in length) onto 560P medium containing N6 salts, Erikkson's vitamins, 0,69 g/l proline, 2 mg/l 2,4-D and 3% sucrose. After 4–5 days of incubation in the dark at 28° C., embryos were removed from 560P medium and cultured, scutellum up, onto 560Y medium which is equivalent to 560P but contains 12% sucrose. Embryos were allowed to acclimate to this medium for 3 h prior to transformation. The scutellar surface of the immature embryos was targeted using particle bomardment with a ubi:moCAH:pinII plasmid (PHP10675). Embryos were transformed using the PDS-1000 Helium Gun from Bio-Rad at one shot per sample using 650PSI rupture disks. DNA delivered per shot averaged at 0.1667 ug. Following bombardment, all embryos were maintained on 560L medium (N6 salts, Eriksson's vitamins, 0.5 mg/l thiamine, 20 g/l sucrose, 1 mg/l 2,4-D, 2.88 g/l proline, 2.0 g/l gelrite, and 8.5 mg/l silver nitrate). After 2–7 days post-bombardment, all the embryos from both treatments were transferred onto N6-based medium containing 50 mg/l cyanamide (Pioneer 560P medium described above, with 50 mg/l cyanamide). Plates were maintained at 28° C. in the dark and were observed for colony recovery with transfers to fresh medium occurring every two to three weeks. Early in the sub-culture regime, GFP+ and GFP– embryos were separated. These two sub-populations were subsequently cultured and analyzed as separate treatments. The PAT~GFP expression cassette and the LEC1 expression cassette co-segregate together, and thus the presence of GFP expression is used to separate LEC1+ and LEC1–progeny for analysis.

As seen in the table below, comparing PAT~GFP+/LEC1+ transgenic embryos with wild-type (non-transgenic) embryos from the same ear showed that the overall recovery of cyanimide-resistant transformants was much higher for the transgenic embryos. For the first ear, a frame-shift control, there was no apparent improvement. For the second and third ears, both expressing a functional LEC1 protein, transformation frequencies increased from 0 (non-transformed) to 21.7% (transgenic) and from 9.1% (non-transformed) to 88.5% (transformed), respectively.

TABLE VI

| T0 transgenes (co-Ear segregating) | # GFP + embryos | # of GFP – embryos | Tnx. Frequency GFP + embryos | Tnx. Frequency GFP – embryos |
|---|---|---|---|---|
| 1 PHP15636 + GFP | 65 | 72 | 3/65 = 4.6% | 3/72 = 4.2% |
| 2 PHP16273 + GFP | 23 | 29 | 5/23 = 21.7% | 0/29 |
| 3 PHP16215 + GFP | 26 | 11 | 23/26 = 88.5% | 1/11 = 9.1% |

What is claimed is:

1. A method for transforming a target plant cell comprising stably transforming the target cell with a growth stimulation polynucleotide operably linked to a promoter functional in a plant to produce a modified cell, growing the modified cell through at least one cell division to produce a progeny cell expressing the growth stimulation polynucleotide, and then transforming the progeny cell with at least one polynucleotide of interest operably linked to a promoter functional in a plant, wherein the growth stimulation polynucleotide comprises a cell cycle stimulatory polynucleotide or a developmental polynucleotide.

2. The method of claim 1 wherein transformation frequency is increased compared to corresponding plant cells that do not contain the growth stimulation polynucleotide.

3. The method of claim 1 wherein the progeny cell is from T0 transgenic cultures, regenerated plants or any subsequent progeny cell.

4. The method of claim 3 wherein the progeny cell is from a T0 regenerated plant or a plant from any subsequent generation expressing the growth stimulation polynucleotide.

5. The method of claim 1 wherein the growth stimulation polynucleotide comprises a geminivirus Replicase nucleic acid.

6. The method of claim 5 wherein the growth stimulation polynucleotide comprises wheat dwarf virus Replicase nucleic acid.

7. The method of claim 1 wherein the growth stimulation polynucleotide comprises a Lec1 nucleic acid.

8. The method of claim 1 wherein the target cell is from a monocot or a dicot plant.

9. The method of claim 1 wherein the target cell is from a monocot.

10. The method of claim 1 wherein the target cell is from a maize plant.

11. The method of claim 1 wherein the target cell is from a dicot.

12. The method of claim 1 wherein the target cell is from a soybean plant.

13. The method of claim 1 wherein the target cell is from corn, soybean, sunflower, sorghum, canola, wheat, alfalfa, cofton, rice, barley, potato, tomato, or millet.

14. A method for increasing transformation efficiency comprising transforming a target plant cell with at least one polynucleotide of interest operably linked to a promoter, wherein the target cell has been previously stably transformed to express a heterologous growth stimulation polynucleotide and has gone through at least one cell division, wherein the growth stimulation polynucleotide comprises a cell cycle stimulatory polynucleotide or a developmental polynucleotide.

15. The method of claim 14 wherein the target cell is from T0 transgenic cultures, regenerated plants or any subsequent progeny cell expressing the transgenic growth stimulation polynucleotide.

16. The method of claim 15 wherein the target cell is from a T0 regenerated plant or any subsequent generation expressing the transgenic growth stimulation potynucleotide.

17. The method of claim 14 wherein the target cell contains a geminivirus Replicase nucleic acid.

18. The method of claim 17 wherein the target cell contains wheat dwarf virus Replicase nucleic acid.

19. The method of claim 14 wherein the target cell contains a Lec1 nucleic acid.

20. The method of claim 14 wherein the target cell is from a monocot or a dicot plant.

21. The method of claim 14 wherein the target cell is from a monocot.

22. The method of claim 14 wherein the target cell is from a maize plant.

23. The method of claim 14 wherein the target cell is from a dicot.

24. The method of claim 14 wherein the target cell is from a soybean plant.

25. The method of claim 14 wherein the target cell is from corn, soybean, sunflower, sorghum, canola, wheat, alfalfa, cotton, rice, barley, potato, tomato, or millet.

26. The method of claim 5 wherein the growth stimulation polynucleotide comprises RepA.

27. The method of claim 18 wherein the growth stimulation polynucleotide comprises RepA.

28. A method for transforming a target plant cell comprising stably transforming the target cell with a growth stimulation polynucleotide operably linked to a promoter functional in a plant to produce a modified cell, growing the modified cell through at least one cell division to produce a progeny cell expressing the growth stimulation polynucleotide, and then transforming the progeny cell with at least one polynucleotide of interest operably linked to a promoter functional in a plant, wherein the growth stimulation polynucleotide comprises RepA or Lec1.

29. A method for increasing transformation efficiency comprising transforming a target plant cell with at least one polynucleotide of interest operably linked to a promoter, wherein the target cell has been previously stably transformed to express a transgenic growth stimulation polynucleotide and has gone through at least one cell division, wherein the growth stimulation polynucleotide comprises RepA or Lec1.

* * * * *